United States Patent [19]

Wise et al.

[11] 4,134,982

[45] Jan. 16, 1979

[54] ANTIPSYCHOTIC 1-[4,4-BIS(4-FLUOROPHENYL)BUTYL]-4-PHENOXY-1,2,3,6-TETRAHYDROPYRIDINES

[75] Inventors: Lawrence D. Wise, Ann Arbor, Mich.; Patrick F. Flynn, Wilmington, Del.; Glenn C. Morrison, Ann Arbor, Mich.

[73] Assignee: Warner-Lambert Company, Morris Plains, N.J.

[21] Appl. No.: 836,867

[22] Filed: Sep. 26, 1977

[51] Int. Cl.$^2$ .................. A61K 31/44; C07D 211/74; C07D 213/69

[52] U.S. Cl. ............................ 424/263; 260/293.75; 260/293.79; 260/293.83; 260/294.9; 260/296 AE; 260/297 R; 424/267

[58] Field of Search ......... 260/297 R, 296 AE, 294.9; 424/263

[56] References Cited

U.S. PATENT DOCUMENTS

| | | | |
|---|---|---|---|
| 3,260,723 | 7/1966 | L'Italien | 260/297 R |
| 3,927,006 | 12/1975 | Edenhofer | 260/297 R |

Primary Examiner—Henry R. Jiles
Assistant Examiner—Richard A. Schwartz
Attorney, Agent, or Firm—Albert H. Graddis; Frank S. Chow; Anne M. Kelly

[57] ABSTRACT

1-[4,4-Bis(4-fluorophenyl)butyl]-4-phenoxy-1,2,3,6-tetrahydropyridines and related piperidines are disclosed in the present invention. These compounds have the structural formulas:

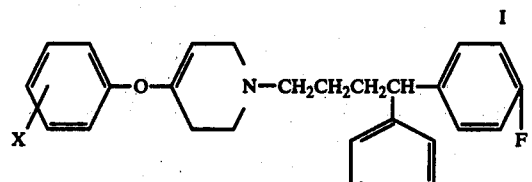

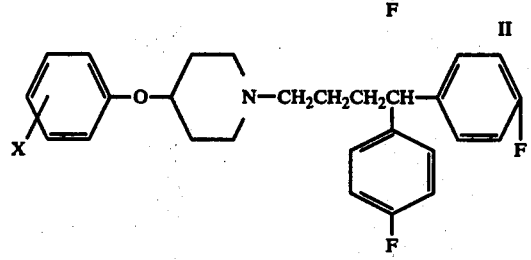

in which X is hydrogen, halogen, dihalogen, trifluoromethyl, lower alkoxy, nitro, amino, cyano, lower alkyl, aryl or substituted aryl. Also included are the corresponding non-toxic, pharmaceutically acceptable acid addition salts, and the N-oxides of compounds of the formulas I and II.

The above compounds are useful in the management of manifestations of psychotic disorders.

36 Claims, No Drawings

ANTIPSYCHOTIC 1-[4,4-BIS(4-FLUOROPHENYL)BUTYL]-4-PHENOXY-1,2,3,6-TETRAHYDROPYRIDINES

The present invention relates to diphenyl butylamines and, more particularly, it relates to 1-[4,4-bis(4-fluorophenyl)butyl]-4-phenoxy-1,2,3,6-tetrahydropyridines and related piperidines, having the formulas:

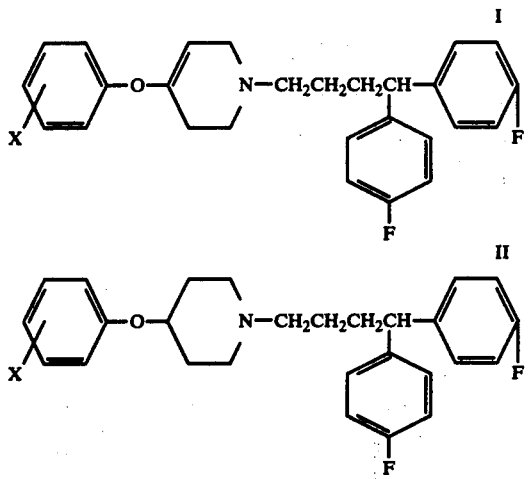

in which X is hydrogen, halogen, dihalogen, trifluoromethyl, lower alkoxy, nitro, amino, cyano, lower alkyl, aryl or substituted aryl. Also included are the corresponding non-toxic, pharmaceutically acceptable acid addition salts and the N-oxides thereof.

Compounds of formulas I and II wherein X is hydrogen, halogen, dihalogen, trifluoromethyl, lower alkoxy, nitro, amino, lower alkyl, phenyl or phenyl substituted by a halogen, nitro, lower alkyl or lower alkoxy group; and the non-toxic, pharmaceutically acceptable acid addition salts thereof are preferred. Especially preferred compounds are those of the formulas I and II wherein X is hydrogen, halogen, dihalogen, trifluoromethyl, lower alkoxy, nitro, lower alkyl or phenyl and the non-toxic, pharmaceutically acceptable acid addition salts thereof.

In the above definition for X, halogen is meant to include all four members, i.e., fluorine, chlorine, bromine and iodine. Lower alkyl and the lower alkyl portion of lower alkoxy has 1 to 6 carbon atoms as exemplified by methyl, ethyl, propyl, isopropyl, butyl, isobutyl and so on. Aryl is preferably an aromatic hydrocarbon of 6 to 10 carbon atoms such as phenyl or naphthyl. The aryl may be optionally substituted by groups such as the aforesaid halogen, dihalogen, nitro, amino, cyano, trifluoromethyl, lower alkyl or lower alkoxy.

The compounds of the present invention, including the salts are indicated in the management of manifestations of psychotic disorders such as reducing excitement, hypermotility and agitation.

In experimental studies such as the shuttle box conditioned procedure described by Robichaud, et al, in *Psychopharmacologia,* 32, 157 (1973), using mice as the host, these compounds exhibited activity in a range of about 5 to 10 mg/kg intraperitoneally.

Generally speaking, in the management of psychotic disorders, the compounds or their salts are administered orally or intramuscularly at 5 to 10 mg per kilogram of the patient's body weight one to three times daily. As with any psychotherapeutic treatment, the dosage must be individualized according to the degree of mental and emotional disturbance of the patient.

Among the dosage forms there may be mentioned, for example, tablets, capsules and injectables. Tablets are prepared by mixing the active ingredient with inert diluants such as lactose, granulated with water and then compressing the dried granules into tablets. Capsules are prepared by mixing the active ingredient with an inert diluant such as lactose, calcium phosphate, mannitol and the like and dispensed in gelatin capsules.

Injectable dosage forms include those suitable for intramuscular injection. These are prepared by mixing the active ingredient with a parenterally acceptable vehicle such as sterile water with suitable suspending agents and then compounded by well-known pharmaceutical technology.

According to the present invention, the above compounds are prepared by treating 4-phenoxypyridine of the formula:

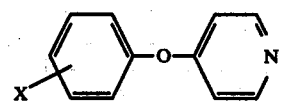

with bis(p-fluorophenyl)butyl chloride and sodium halide to obtain quaternary salts of formula IV.

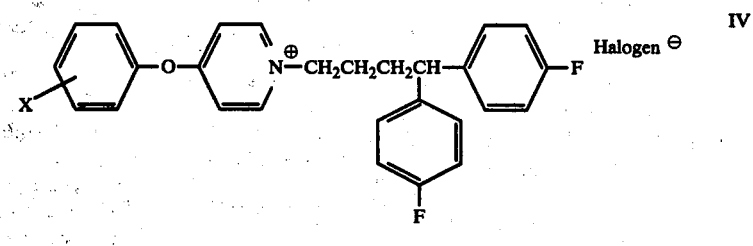

The quaternary ammonium salts IV are intermediates useful in preparing the final compounds I and II of this invention. Thus, the quaternary ammonium salts IV may be partially reduced by a complex metal hydride, e.g. sodium borohydride, to give the tetrahydropyridines of formula I.

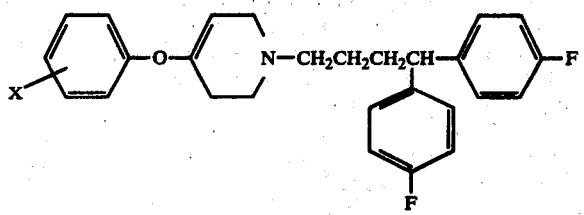

Alternately, the pyridinium salts IV may be totally reduced to piperidines II by catalytic hydrogenation, e.g. with a reducing catalyst such as platinum oxide or 10% palladium-on-carbon, at 50 psi.

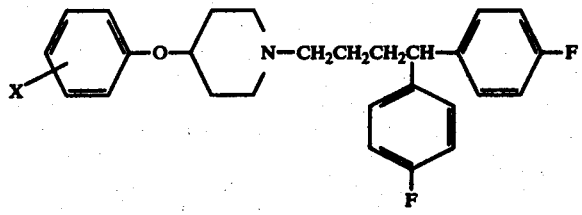

Starting Compound III is synthesized according to the teachings disclosed in U.S. Pat. No. 3,260,723.

The pharmacologically acceptable acid addition salts of the present invention are prepared by treating Compounds I or II with an acid such as hydrochloric, hydrogen iodide, nitric, sulfuric, oxalic, tartaric and the like in stoichiometric amounts. Of these, the tartaric acid salts are preferred i.e. the D,L-tartarates or the d-tartarates; the d-tartarates are especially preferred. These salts are recovered by methods known in the art.

Finally, the N-oxides of the present invention are obtained by treating Compounds I and II with an oxidizing agent such as hydrogen peroxide.

In order to illustrate the practice of the present invention, the following examples are included:

EXAMPLE 1

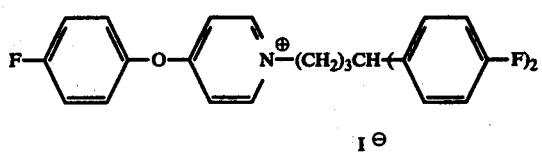

4-(4-Fluorophenoxy)-1-[4,4-bis(4-fluorophenyl)-butyl]-pyridinium iodide. A solution of 8.2 g of 4-(4-fluorophenoxy)pyridine, 12.2 g of 1,1'-(4-chlorobutylidine)bis-[4-fluorobenzene] and 13.0 g of sodium iodide in 300 ml of methyl ethyl ketone is refluxed for 20 hrs. The solvent is removed in vacuo and the residue washed successively with ether and water. The product is recrystallized from isopropanol to afford 15.5 g (67%) of pale orange needles, m.p. 176–177° C.

Anal. Calcd. for $C_{27}H_{23}F_3INO$: C, 57.77; H, 4.13; F, 10.15; N, 2.50; I, 22.61. Found: C, 57.56; H, 4.25; F, 10.41; I, 22.68.

Employing the procedure described in the above example, the following compounds were also prepared:

TABLE I

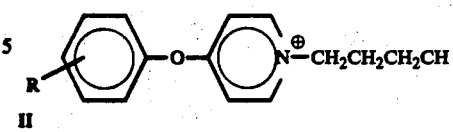

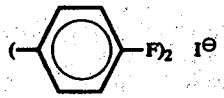

| R | Formula | Analysis | Mp |
|---|---|---|---|
| H | $C_{27}H_{24}F_2INO$ | CHFIN | 153–154° C. |
| p-Cl | $C_{27}H_{23}ClF_2INO$ | CHClFIN | 138–140° C. |
| p-C(CH$_3$)$_2$ | $C_{31}H_{32}F_2INO$ | CHFIN | 189–191° C. |
| p-C$_6$H$_5$ | $C_{33}H_{28}F_2INO$ | CHFIN | 144–146° C. |
| p-CF$_3$ | $C_{28}H_{23}F_5INO$ | CHFIN | 183–185° C. |
| p-CH$_3$ | $C_{28}H_{26}F_2INO$ | CHFIN | 123–125° C. |
| p-OCH$_3$ | $C_{28}H_{26}F_2INO_2$ | CHFIN | 120–122° C. |
| m,p-Cl,Cl | $C_{27}H_{22}Cl_2F_2INO$ | CHClFIN | 148–150° C. |
| o,o-Cl,Cl | $C_{27}H_{23}F_2IN_2O_3$ | CHFIN | 212–213° C. |
| p-NO$_2$ | $C_{27}H_{23}ClF_2INO$ | CHClFIN | 146–148° C. |
| m-Cl | $C_{27}H_{23}ClF_2INO$ | CHClFIN | 140–141° C. |
| o-Cl | $C_{27}H_{23}ClF_2INO$ | CHClFIN | 105–107° C. |
| m-OCH$_3$ | $C_{28}H_{26}F_2INO_2$ | CHFIN | 159–160° C. |
| o-OCH$_3$ | $C_{28}H_{26}F_2INO_2$ | CHFIN | 120–122° C. |

EXAMPLE 2

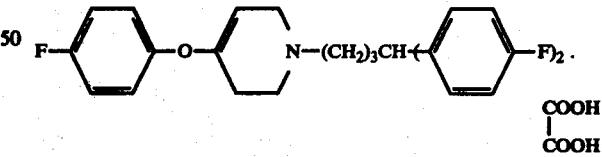

4-(4-Fluorophenoxy)-1-[4,4-bis(4-fluorophenyl)-butyl]-1,2,3,6-tetrahydropyridine ethanedioate. To a solution of 2.8 g of 4-(4-fluorophenoxy)-1-[4,4-bis(4-fluorophenyl)butyl]-pyridinium iodide in 200 ml of methanol was added portionwise with stirring 0.57 g of sodium borohydride at 0–10° C. After 15 min., the solvent is removed in vacuo. The residue is taken up in ether and passed through a bed of florisil. Treatment of the filtrate with ethereal oxalic acid afforded 2.1 g (64%) of white powder, m.p. 180–182° C.

Anal. Calcd. for $C_{27}H_{26}F_3NO\cdot C_2H_2O_4$: C, 66.03; H, 5.35; F, 10.80; N, 2.66. Found: C, 65.76; H, 5.44; F, 10.63; N, 2.61.

Employing the procedure described in the above example, the following compounds were also prepared:

TABLE II

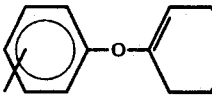

| R | Formula | Analysis | Mp | Acid Salt |
|---|---|---|---|---|
| H | $C_{27}H_{27}F_2NO \cdot C_4H_6O_6$ | CHFN | 140–141° C. | D,L-2,3-dihydroxybutanedioate |
| p-Cl | $C_{27}H_{26}ClF_2NO \cdot C_4H_6O_6$ | CHClFN | 165–167° C. | D,L-2,3-dihydroxybutanedioate |
| p-CF$_3$ | $C_{28}H_{26}F_5NO \cdot C_4H_6O_6$ | CHFN | 149–151° C. | D,L-2,3-dihydroxybutanedioate |
| p-CH$_3$ | $C_{28}H_{29}F_2NO \cdot C_4H_6O_6$ | CHFN | 168–170° C. | d-2,3-dihydroxybutanedioate |
| p-C(CH$_3$)$_3$ | $C_{31}H_{35}F_2NO \cdot C_4H_6O_6$ | CHFN | 141–143° C. | D,L-2,3-dihydroxybutanedioate |
| p-C$_6$H$_5$ | $C_{33}H_{31}F_2NO \cdot C_2H_2O_4$ | CHFN | 196–198° C. | ethanedioate |
| p-OCH$_3$ | $C_{28}H_{29}F_2NO_2 \cdot C_4H_6O_6$ | CHFN | 172–174° C. | d-2,3-dihydroxybutanedioate |
| o,o-Cl,Cl | $C_{27}H_{25}Cl_2F_2NO \cdot C_2H_2O_4$ | CHClFN | 192–194° C. | ethanedioate |
| m,p-Cl,Cl | $C_{27}H_{25}Cl_2F_2NO \cdot C_4H_6O_6$ | CHClFN | 158–160° C. | d-2,3-dihydroxybutanedioate |
| p-NO$_2$ | $C_{27}H_{26}F_2N_2O_3 \cdot C_4H_6O_6$ | CHFN | 170–171° C. | d-2,3-dihydroxybutanedioate |
| m-Cl | $C_{27}H_{26}ClF_2NO \cdot C_4H_6O_6$ | CHClFN | 123–124° C. | d-2,3-dihydroxybutanedioate |
| o-Cl | $C_{27}H_{26}ClF_2NO \cdot C_2H_2O_4$ | CHClFN | 184–185° C. | ethanedioate |
| m-OCH$_3$ | $C_{28}H_{29}F_2NO_2 \cdot C_2H_2O_4$ | CHFN | 190–191° C. | ethanadioate |
| o-OCH$_3$ | $C_{28}H_{29}F_2NO_2 \cdot C_2H_2O_4$ | CHFN | 161–163° C. | ethanedioate |
| p-F | $C_{27}H_{26}F_3NO \cdot C_4H_6O_6$ | CHFN | 152–154° C. | D,L-2,3-dihydroxybutanedioate |
| p-F | $C_{27}H_{26}F_3NO \cdot C_4H_6O_6$ | CHFN | 164–166° C. | d-2,3-dihydroxybutanedioate |

EXAMPLE 3

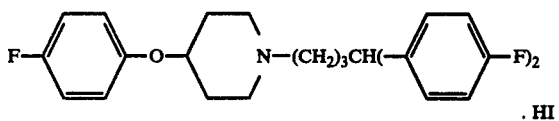

4-(4-Fluorophenoxy)-1-[4,4-bis(4-fluorophenyl)-butyl]-piperidine Hydroidide. A solution of 7.5 g of 4-(4-fluorophenoxy)-1-[4,4-bis(4-fluorophenyl)butyl]-pyridinium iodide in 250 ml of methanol is hydrogenated over ~1 g of PtO$_2$ at an initial pressure of 50 psi for 18 hrs. The catalyst is removed by filtration, and the solvent is evaporated in vacuo. Treatment of the residue with methylene chloride - hexane afforded 3.9 g (68%) of light tan powder, m.p. 133–135° C. The product is recrystallized twice from isopropanol and washed with ether to yield an off-white powder, m.p. 155°–157° C.

Anal. Calcd. for $C_{27}H_{28}F_3NO \cdot HI$: C, 57.15; H, 5.15; F, 10.04; N, 2.47; I, 22.36. Found C, 57.17; H, 5.18; F, 9.75; N, 2.43; I, 22.40.

We claim:

1. A member selected from the group consisting of compounds of the formula:

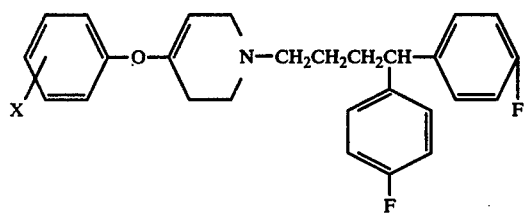

wherein X is hydrogen, halogen, dihalogen, trifluoromethyl, lower alkoxy, nitro, amino, cyano, lower alkyl, phenyl or phenyl substituted by halogen, dihalogen, lower alkyl, lower alkoxy, nitro, cyano, amino or trifluoromethyl; and the corresponding non-toxic, pharmaceutically acceptable acid salts and the N-oxides thereof.

2. The compound according to claim 1 which is 4-(4-fluorophenoxy)-1-[4,4-bis(4-fluorophenyl)butyl]-1,2,3,6-tetrahydropyridine ethanedioate.

3. The compound according to claim 1 which is 1-[4,4-bis-(4-fluorophenyl)butyl]-1,2,3,6-tetrahydro-4-phenoxypyridine D,L-2,3-dihydroxybutanedioate.

4. The compound according to claim 1 which is 4-(4-chlorophenoxy)-1-[4,4-bis(4-fluorophenyl)butyl]-1,2,3,6-tetrahydropyridine D,L-2,3-dihydroxybutanedioate.

5. The compound according to claim 1 which is 1-[4,4-bis(4-fluorophenyl)butyl]-1,2,3,6-tetrahydro-4-(4-trifluoromethyl)-phenoxypyridine D,L-2,3-dihydroxybutanedioate.

6. The compound according to claim 1 which is 1-[4,4-bis(4-fluorophenyl)butyl]-1,2,3,6-tetrahydro-4-(4-methoxyphenoxy)-pyridine d-2,3-dihydroxybutanedioate.

7. The compound according to claim 1 which is 4-[4-(1-1-dimethylethyl)phenoxy]-1-[4,4-bis(p-fluorophenyl)]-1,2,3,6-tetrahydropyridine D,L-2,3-dihydroxybutanedioate.

8. The compound according to claim 1 which is 4-([1,1'-biphenyl]-4-yloxy)-1-[4,4-bis(4-fluorophenyl)-butyl]-1,2,3,6-tetrahydropyridine ethanedioate.

9. The compound according to claim 1 which is 1-[4,4-bis-(4-fluorophenyl)butyl]-1,2,3,6-tetrahydro-4-(4-methoxyphenoxy)-pyridine d-2,3-dihydroxybutanedioate.

10. The compound according to claim 1 which is 4-(2,6-dichlorophenoxy)-1-[4,4-bis(4-fluorophenyl)-butyl]-1,2,3,6-tetrahydropyridine ethanedioate.

11. The compound according to claim 1 which is 4-(3,4-dichlorophenoxy)-1-[4,4-bis(4-fluorophenyl)-butyl]-1,2,3,6-tetrahydropyridine d-2,3-dihydroxybutanedioate.

12. The compound according to claim 1 which is 4-(4-nitrophenoxy)-1-[4,4-bis(4-fluorophenyl)butyl]-1,2,3,6-tetrahydropyridine d-2,3-dihydroxybutanedioate.

13. The compound according to claim 1 which is 4-(3-chlorophenoxy)-1-[4,4-bis(4-fluorophenyl)butyl]-1,2,3,6-tetrahydropyridine d-2,3-dihydroxybutanedioate.

14. The compound according to claim 1 which is 4-(2-chlorophenoxy)-1-[4,4-bis(4-fluorophenyl)butyl]-1,2,3,6-tetrahydropyridine ethanedioate.

15. The compound according to claim 1 which is 4-(3-methoxyphenoxy)-1-[4,4-bis(4-fluorophenyl)-butyl]-1,2,3-tetrahydropyridine ethanedioate.

16. The compound according to claim 1 which is 4-(2-methoxyphenoxy)-1-[4,4-bis(4-fluorophenyl)-butyl]-1,2,3,6-tetrahydropyridine ethanedioate.

17. The compound according to claim 1 which is 4-(4-fluorophenoxy)-1-[4,4-bis(4-fluorophenyl)butyl]-1,2,3,6-tetrahydropyridine D,L-2,3-dihydroxybutanedioate.

18. The compound according to claim 1 which is 4-(4-fluorophenoxy)-1-[4,4-bis(4-fluorophenyl)butyl]-1,2,3,6-tetrahydropyridine d-2,3-dihydroxybutanedioate.

19. A pharmaceutical composition for the treatment of manifestations of psychotic disorders in mammals comprising a psychotherapeutically effective amount of a member selected from the group consisting of compounds of the formula:

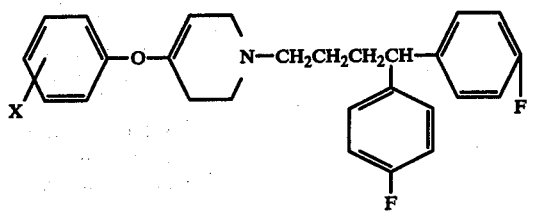

I wherein X is hydrogen, halogen, dihalogen, trifluoromethyl, lower alkoxy, nitro, amino, cyano, lower alkyl, phenyl or phenyl substituted by halogen, dihalogen, lower alkyl, lower alkoxy, nitro, cyano, amino or trifluoromethyl; and the corresponding non-toxic, pharmaceutically acceptable acid salts and the N-oxides thereof; together with an inert pharmaceutical carrier therefor.

20. A method for treating the manifestations of psychotic disorders in mammals which comprises the administration of a psychotherapeutically effective amount of a member selected from the group consisting of compounds of the formula:

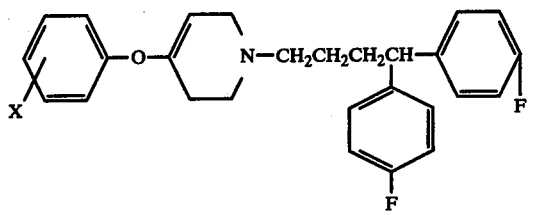

I wherein X is hydrogen, halogen, dihalogen, trifluoromethyl, lower alkoxy, nitro, amino, cyano, lower alkyl, phenyl or phenyl substituted by halogen, dihalogen, lower alkyl, lower alkoxy, nitro, cyano, amino or trifluoromethyl; and the corresponding non-toxic, pharmaceutically acceptable acid salts and the N-oxides thereof.

21. A compound of the formula IV:

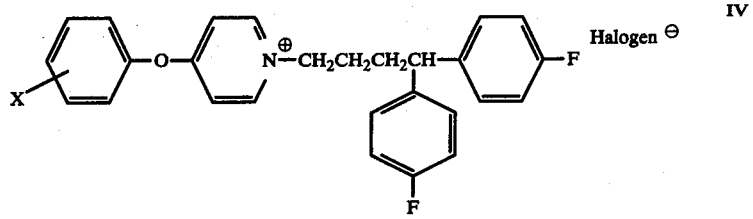

IV wherein X is hydrogen, halogen, dihalogen, trifluoromethyl, lower alkoxy, nitro, amino, cyano, lower alkyl, phenyl, or phenyl substituted by halogen, dihalogen, lower alkyl, lower alkoxy, nitro, cyano, amino or trifluoromethyl.

22. The compound according to claim 21 which is 4-(4-fluorophenoxy)-1-[4,4-bis(4-fluorophenyl)butyl]-pyridinium iodide.

23. The compound according to claim 21 which is 1-[4,4-bis-(4-fluorophenyl)butyl]-4-phenoxy-pyridinium iodide.

24. The compound according to claim 21 which is 4-(4-chlorophenoxy)-1-[4,4-bis(4-fluorophenyl)butyl]-pyridinium iodide.

25. The compound according to claim 21 which is 4-[4-(1,1-dimethylethyl)phenoxyl]-1-[4,4-bis(4-fluorophenyl)butyl]pyridinium iodide.

26. The compound according to claim 21 which is 4-([1,1'-biphenyl]-4-yloxy)-1-[4,4-bis(4-fluorophenyl)-butyl]pyridinium iodide.

27. The compound according to claim 21 which is 1-[4,4-bis(4-fluorophenyl)butyl]-4-[4-(trifluoromethyl)-phenoxy]pyridinium iodide.

28. The compound according to claim 21 which is 1-[4,4-bis-(4-fluorophenyl)butyl]-4-(4-methylphenoxy)-pyridinium iodide.

29. The compound according to claim 21 which is 1-[4,4-bis-(4-fluorophenyl)butyl]-4-(4-methoxyphenoxy)pyridinium iodide.

30. The compound according to claim 21 which is 4-(3,4-dichlorophenoxy)-1-[4,4-bis(4-fluorophenyl)-butyl]pyridinium iodide.

31. The compound according to claim 21 which is 4-(2,6-dichlorophenoxy)-1-[4,4-bis(4-fluorophenyl)-butyl]pyridinium iodide.

32. The compound according to claim 21 which is 1-[4,4-bis-(4-fluorophenyl)butyl]-4-(4-nitrophenoxy)-pyridinium iodide.

33. The compound according to claim 21 which is 4-(3-chlorophenoxy)-1-[4,4-bis(4-fluorophenyl)butyl]-pyridinium iodide.

34. The compound according to claim 21 which is 4-(2-chlorophenoxy)-1-[4,4-bis(4-fluorophenyl)butyl]-pyridinium iodide.

35. The compound according to claim 1 which is 4-(3-methoxyphenoxy)-1-[4,4-bis(4-fluorophenyl)-butyl]pyridinium iodide.

36. The compound according to claim 21 which is 4-(2-methoxyphenoxy)-1-[4,4-bis(4-fluorophenyl)-butyl]pyridinium iodide.